(12) United States Patent
Ranga et al.

(10) Patent No.: US 8,227,590 B2
(45) Date of Patent: Jul. 24, 2012

(54) HIGH SENSITIVITY ASSAY FOR MOLECULAR TYPING OF BIOLOGICAL SAMPLE, PROBES AND A KIT THEREOF

(75) Inventors: Udaykumar Ranga, Karnataka (IN); Chandrabhas Narayana, Karnataka (IN); Jayasuryan Narayana, Karnataka (IN)

(73) Assignees: Jawaharlal Nehru Centre for Advanced Scientific Research, Karnataka (IN); Microtest Innovations Pvt. Ltd., Karnataka (IN)

( * ) Notice: Subject to any disclaimer, the term of this patent is extended or adjusted under 35 U.S.C. 154(b) by 175 days.

(21) Appl. No.: 12/515,766

(22) PCT Filed: Nov. 19, 2007

(86) PCT No.: PCT/IN2007/000543
§ 371 (c)(1),
(2), (4) Date: May 21, 2009

(87) PCT Pub. No.: WO2008/062479
PCT Pub. Date: May 29, 2008

(65) Prior Publication Data
US 2010/0028858 A1    Feb. 4, 2010

(30) Foreign Application Priority Data
Nov. 21, 2006  (IN) .......................... 02161/CHE/2006

(51) Int. Cl.
*C07H 21/04*    (2006.01)
*C12Q 1/68*    (2006.01)
(52) U.S. Cl. ................................... 536/24.32; 435/6.12

(58) Field of Classification Search ............... 536/24.32; 435/6, 6.12
See application file for complete search history.

(56) References Cited

U.S. PATENT DOCUMENTS

| 5,871,902 A | * | 2/1999 | Weininger et al. | 435/5 |
| 6,015,661 A | * | 1/2000 | Deacon et al. | 435/5 |
| 2003/0039636 A1 | | 2/2003 | Leboulch et al. | |
| 2004/0086897 A1 | | 5/2004 | Mirkin et al. | |
| 2006/0204500 A1 | | 9/2006 | June et al. | |

FOREIGN PATENT DOCUMENTS

| WO | WO 99/27140 | 6/1999 |
| WO | WO 2005/116250 | 12/2005 |

OTHER PUBLICATIONS

International Preliminary Report mailed on Apr. 24, 2009 in corresponding PCT Patent Application No. PCT/IN2007/000543 filed Nov. 19, 2007.
Cao et al. (2002), Science, vol. 297 (5586): 1536-40.
Accession No. AY822655. HIV-1 isolate 04/365 from India LTR, partial sequence (2005).
Accession No. AF388991. HIV-1 isolate 99ZA42ZA from South Africa 5' long terminal repeat, partial sequence (2001).

* cited by examiner

*Primary Examiner* — Prabha Chunduru
(74) *Attorney, Agent, or Firm* — Kilpatrick Townsend & Stockton LLP

(57) ABSTRACT

The present invention relates to a high sensitivity assay for molecular typing of a biological sample using surface-enhanced Raman scattering (SERS) including resonance scattering (SERRS); capture probes for capturing nucleic acid; a detector probe to detect captured nucleic acid; a kit for molecular typing of biological sample using surface-enhanced Raman scattering (SERS) including resonance scattering (SERRS); and lastly a method of manufacturing said kit.

9 Claims, 5 Drawing Sheets

Capture probe

B-virus

B

C

Figure 1:
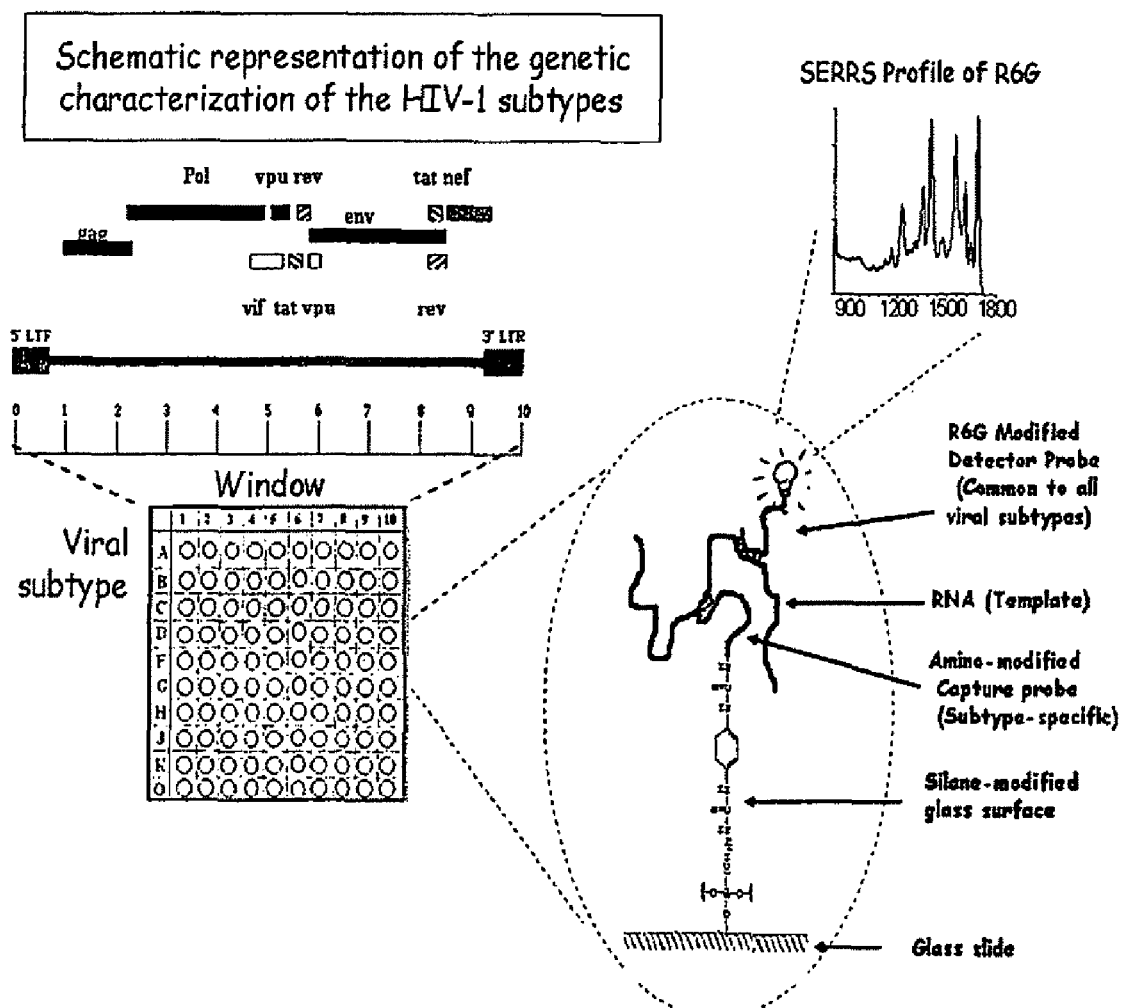

HIGH SENSITIVITY ASSAY FOR MOLECULAR TYPING OF BIOLOGICAL SAMPLE, PROBES AND A KIT THEREOF

CROSS-REFERENCE TO RELATED APPLICATIONS

This application is a National Stage of International Application No. PCT/IN2007/000543, filed Nov. 19, 2007, which in turn claims priority to and the benefit of Indian Patent Application No. 02161/CHE/2006, filed on Nov. 21, 2006, the disclosures of which are expressly incorporated herein by reference in their entirety.

FIELD OF THE INVENTION

The present invention relates to a field of high sensitivity assay for molecular typing of biological sample using surface-enhanced Raman scattering, including resonance scattering. The invention also relates to capture probes, detector probes, a kit for molecular typing of biological sample and a method of manufacturing the kit.

BACKGROUND OF THE INVENTION

HIV/AIDS has become a serious global health hazard at a dimension unprecedented by any other infection. Human Immunodeficiency Virus type-1 (HIV-1) exhibits extremely high degree of variation at genetic level (Leitner et al., 2005). Based on the genetic homology, HIV-1 is classified into 9 distinct and primary genetic subtypes designated A through J (with the exception of E and I which are recombinants). Distribution of the viral subtypes across the globe is non-uniform. Additionally, epidemic outbreaks due to recombinant forms of the viruses are also becoming a serious problem in several geographical regions.

In addition to the above mentioned primary viral subtypes, a large number of recombinant viruses have been identified globally. Recombinant viruses arise when a genetic exchange takes place between two or more different viral strains generating a novel recombinant form (Najera et al., 2002). Depending on the epidemiologic incidence, recombinant viruses are of two types. First, circulating recombinant forms (CRF) are strains that have established successful infection in a geographical region or population and been characterized at the molecular level. The A/E virus of Thailand is one such recombinant virus. Second, the unique recombinant forms (URF), viruses that have been isolated from limited number of subjects and not adequately characterized at the molecular level. The incidence of global viral infections due to both the recombinant forms is on the rise at an alarmingly exponential rate. The total numbers of molecularly characterized CRFs has increased to 34 presently from 8 during the past 2-3 years. On the other hand, a large number of URFs are being identified on a regular basis. Generation and expansion of the recombinant viruses may throw serious challenges at disease intervention strategies like vaccine development and drug therapy (Najera et al., 2002; Lal et al., 2005; Peeters, 2000). It is therefore important to develop simple and inexpensive diagnostic strategies to detect recombinant viruses on a priority basis.

The objective of the present invention is to develop a novel and innovative strategy to detect primary subtypes and recombinant strains of HIV, preferably HIV-1. The same strategy is useful in assaying other types of viruses, bacteria, fungi, protozoa and parasites.

The assay is applicable to any kind of nucleic acids isolated from any kind of biological source including RNA and DNA without amplification.

PRIOR ART OF THE INVENTION

Detection of HIV has also been approached by some of the known techniques which are discussed below with their limitations.

A) Full-genome sequencing: Determination of the complete nucleic acid sequence is the golden standard for subtype determination of a viral strain (Peeters, 2000; Carr et al., 1999). This strategy can molecularly characterize not only the standard viral subtypes and the existing recombinant forms but also any novel recombinant viruses that may emerge in future.

Shortcoming of the technique: Despite its universal and broad range appeal, this strategy is too expensive, labor intensive and can not be applied to a large number of samples. This strategy is applied only to a small number of selected samples and unsuitable for a large-scale epidemiological study. Importantly, since sequencing is often performed following PCR amplification of the target sequence, false positive results can not be avoided especially in situation where sophisticated diagnostic laboratories are not available (Kwok and Higuchi, 1989; Rys and Persing, 1993; Scherczinger et al., 1999; Wilke et al., 1995). The bulk of the viral infections occur in poor countries with limited technical resources. False positive result could be a serious technical limitation in these countries.

B) Multi-region hybridization assay (MHA): This assay is presently the most widely employed for subtype characterization of HIV-1 (Hoelscher et al., 2002; Herbinger et al., 2006). The assay is based on the real-PCR strategy (Niesters, 2001; Espy et al., 2006) using a set of well characterized TaqMan probes (Yeung et al., 2004; Desire et al., 2001). The TaqMan probes are designed to target distinct sequences (usually 5-7 windows) across the length of the virus and of defined viral subtypes (usually 2 or 3) (Hoelscher et al., 2002; Herbinger et al., 2006; Gerhardt et al., 2005). Each probe is linked to two different fluorescent dyes one a reporter and the other a quencher. Depending on the pattern of report signal generated for the individual windows, the subtype nature of a viral strain can be determined.

Shortcoming of the technique: The technique is relatively less expensive than full-length genome sequencing. Additionally, it can be applied to relatively larger number of samples. The technique, however, suffers from several technical problems. There are multiple problems with the technique. First, the technique practically can not be used to analyze more than 2 or 3 different viral subtypes. A prior knowledge of the viral subtypes in circulation in a given context is necessary for assay design. Second, the assay can not target a large number of windows with the virus. Usually 5-7 windows are targeted. A total of 15 individual TaqMan probes will be required to analyze 3 different subtype and 5 individual windows in each subtype. Given that four individual primers are required (due to the nested-PCR format employed) for each amplification, the assay will require a total of 60 primers and 15 TaqMan probes to molecularly characterize three different viral subtypes. This will be enormously expensive and labor-intensive and as a consequence, practically of limited application. Third, the assay will fail to detect a recombinant or a subtype that is not targeted by the experimental scheme. Fourth, since the technique invariably requires target amplification, false positive results are a serious concern (see above).

C) Branched DNA (bDNA) technology: This technology is identical in one important aspect to our novel strategy described below. It is for this similarity this technique is being quoted here although the main objective of this technique is not to molecularly characterize diverse subtypes and recombinants of HIV-1, but to determine the viral load in biological samples. Like our technique described below, bDNA does not amplify the target viral RNA or DNA but captures the nucleic acid using a capture probe and cross-links it to a plastic surface in a micro titer plate. The technique involves the application of a complex network of detector probes that cross link a large number of alkaline phosphatase enzyme to the captured nucleic acid. The technique finally uses the enzyme activity and the read out is the development of color and is akin to the Enzyme-linked immunosorbent assay (ELISA). The technique compensates for lack of target amplification by recruiting a large number of enzyme molecules. A commercial kit is marketed by Chiron Diagnostics using this technique (Kern et al., 1996; Collins et al., 1997).

The strategy of capturing viral RNA in our invention and the bDNA technology differ from each other in the design of the capture probe and importantly in subsequent detection technology following target capture. While bDNA uses an enzyme to develop a signal, our strategy employs SERS. Unlike bDNA technique, our technique is technically less complicated, more sensitive and economical. Further, the primary objectives of these two techniques are quite different. While bDNA is mainly designed for viral load determination, our technique is developed for the molecular characterization of the viral subtypes and recombinants.

D) DNA array detection of Hepatitis virus RNA: In this publication, the authors attempted to detect Hepatitis A virus in sewage samples (Wan et al., 2005). The virus was sedimented, viral RNA reverse transcribed and PCR amplified. The amplified DNA was captured to glass surface using a chemically cross-linked capture probe and detected using a gold nanoparticle conjugated oligonucleotide. Additionally, they used silver enhancement technique to improve the assay sensitivity. This assay is similar to the strategy developed by us in capturing and detecting a target nucleic acid using a capture probe and a detector probe. However, our strategy employs diction of a sensitive Raman reporter rather than a gold nonoparticle. Also our strategy doesn't require PCR amplification but direct capture of the viral RNA. Additionally, our strategy is characterized by targeting multiple windows of the same target thus offering the advantage of detection of recombinant viruses and multiplexing that could eliminate the possibility of false negative results.

E) Other techniques: A range of several other techniques can be used for viral subtype determination. These techniques include the heteroduplex mobility assay (HMA) (Delwart et al., 1993; Heyndrickx et al., 2000), restriction length fragment polymorphism (RFLP) (van Harmelen et al., 1999), sequencing of short genome segments (Barbosa et al., 1998) subtype-specific polymerase chain reaction (Peeters et al., 1998) and others (Abravaya et al., 2000; de Baar et al., 2001; Luo et al., 1998; Robbins et al., 1999). Most of these technique have limited application in molecular typing of the viral strains as they are too cumbersome, fail to target diverse viral subtypes, lead to contamination problem and/or expensive.

Tuan Vo Dinh et. al (Anal. Chem. 1998, 70, 1352-1356) and Tuan Vo-Dinh et. al (J. Raman spectrosc.2005; 36: 640-647) reports the use of SERS-active labels for primers used in polymerase chain reaction amplification of specific target DNA sequences for HIV detection. Here, multiple primers are required to be tagged in addition to amplification which will be expensive, laborious and time-consuming.

Our strategy in the present invention doesn't require amplification of target nucleic acids, avoids false-positive/false-negative results and is inexpensive. It requires the use of a single probe tagged to a Raman Reporter. Further, we adsorb the detector probe on to the silver nanoparticles which functions as an enhancement factor as well as not to hinder Raman signal emission.

The present invention relates to a high sensitivity assay for molecular typing of a biological sample using surface-enhanced Raman scattering (SERS) including resonance scattering (SERRS), wherein said assay comprising steps of:
a) extracting nucleic acid from the biological sample;
b) capturing the extracted nucleic acid in a microarray format using subtype-specific and window-specific capture probe(s); and
c) detecting the captured nucleic acid with a detector probe tagged to a reporter to determine molecular typing, subtypes and recombinants on the basis of pattern of signals generated.

OBJECTS OF THE INVENTION

The main object of the present invention is to develop a high sensitivity assay for molecular typing of a biological sample using surface-enhanced Raman scattering (SERS) including resonance scattering (SERRS).

Another main object of the present invention is to develop a high sensitivity assay for molecular typing of HIV.

Yet another object of the present invention is to develop a high sensitivity assay which avoids false-positive/false-negative results and is inexpensive.

Still another object of the present invention is to design capture probes for capturing the nucleic acid, wherein the nucleic acid is either DNA or RNA.

Still another object of the present invention is to design a detector probe to detect captured nucleic acid, wherein the nucleic acid is either DNA or RNA.

Still another object of the present invention is to develop a kit for molecular typing of biological sample.

Still another object of the present invention is to develop a method of manufacturing a kit for molecular typing of biological sample.

STATEMENT OF THE INVENTION

Accordingly, the present invention relates to a high sensitivity assay for molecular typing of a biological sample using surface-enhanced Raman scattering (SERS) including resonance scattering (SERRS), wherein said assay comprising steps of: (a) extracting nucleic acid from the biological sample; (b) capturing the extracted nucleic acid in a microarray format using subtype-specific and window-specific capture probe(s); and (c) detecting the captured nucleic acid with a detector probe tagged to a reporter to determine molecular typing, subtypes and recombinants on the basis of pattern of signals generated; a high sensitivity assay for molecular typing of HIV using surface-enhanced Raman scattering (SERS) including resonance scattering (SERRS), wherein said assay comprising steps of: (a) extracting nucleic acid from the HIV; (b) capturing the extracted nucleic acid in a microarray format using subtype-specific and window-specific capture probe(s); and (c) detecting the captured nucleic acid with a detector probe tagged to a reporter to determine molecular typing, subtypes and recombinants on the basis of pattern of signals generated; Capture probes of SEQ ID NO: 1, SEQ ID NO: 2 and SEQ ID NO: 3 for capturing nucleic acid isolated from biological sample, wherein the capture probes are sub-type specific and window specific; a detector probe of SEQ ID NO:

4 to detect captured nucleic acid, wherein the detector probe is non-specific and identifies all subtypes. a kit for molecular typing of biological sample using surface-enhanced Raman scattering (SERS) including resonance scattering (SERRS), wherein the kit comprising: (a) reagents and buffers to extract nucleic acid from the biological sample; (b) capture probes to capture the nucleic acid; (c) microarray plate to spot capture probes; (d) detector probe to detect capture probe; (e) reporter, preferably Raman reporter; and (f) device to detect pattern of signals generated from microarray; and a method of manufacturing a kit for molecular typing of biological sample using surface-enhanced Raman scattering (SERS) including resonance scattering (SERRS), wherein the method comprising: (a) providing reagents and buffers in the kit to extract nucleic acid from the biological sample; (b) providing appropriate capture probes in the kit to capture the extracted nucleic acid; (c) providing microarray plate in the kit to spot the capture probes; (d) providing detector probe in the kit to detect the capture probe; (e) providing reporter, preferably Raman Reporter; and (f) providing device to detect pattern of signals generated from microarray to manufacture the kit.

BRIEF DESCRIPTION OF ACCOMPANYING DRAWINGS

FIG. 1: Schematic representation of HIV-1 molecular characterization.

Figure 2:
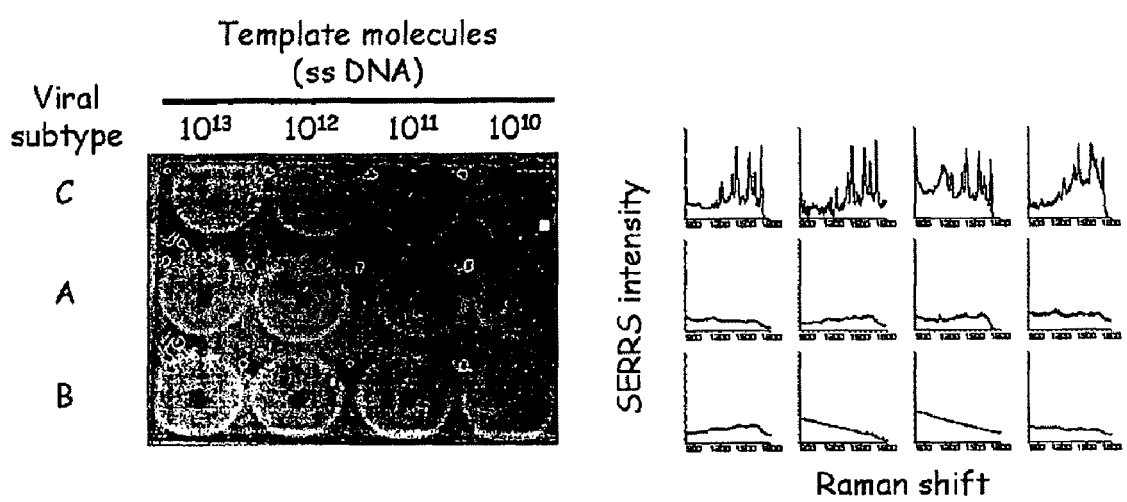

FIG. 2: showing subtype-C capture probe captures homologous but not heterologous viral DNA.

Figure 3:
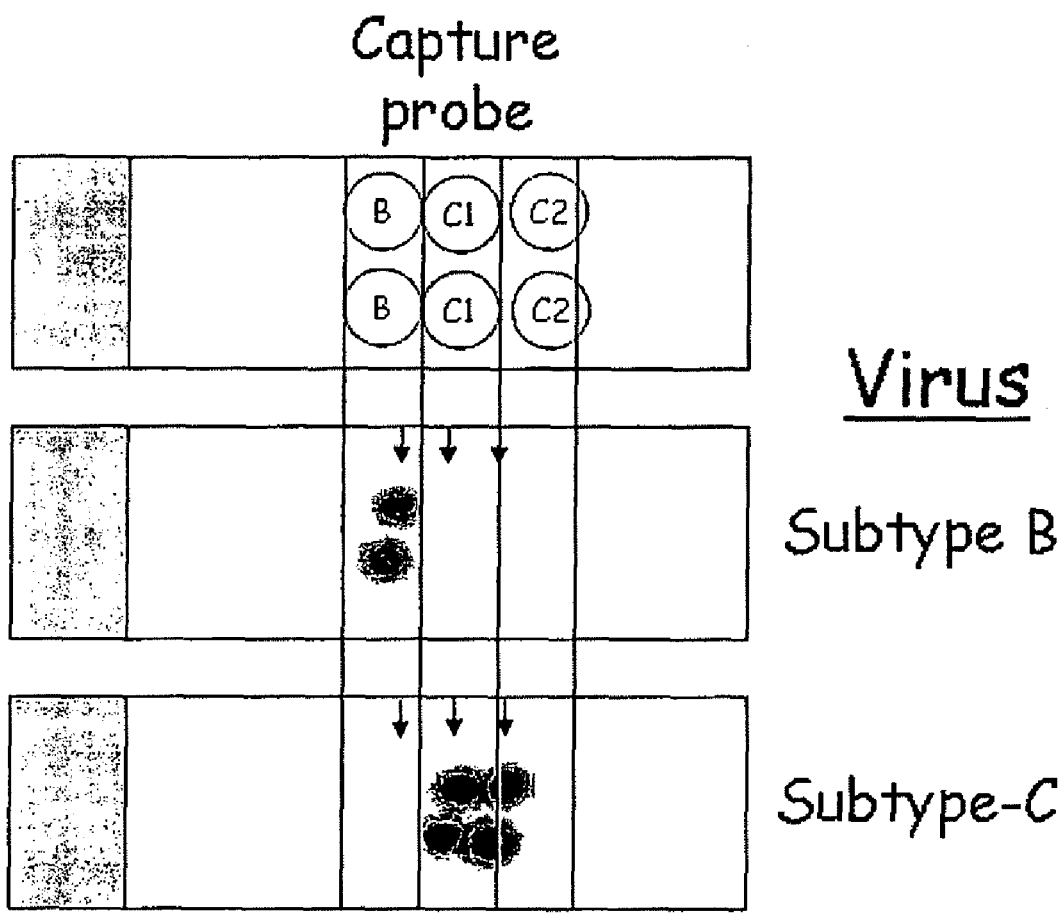

FIG. 3: confirming subtype-specificity of the capture probes.

Figure 4:
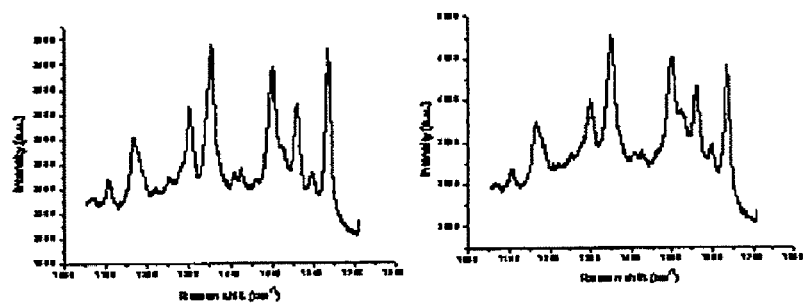
Figure 4:
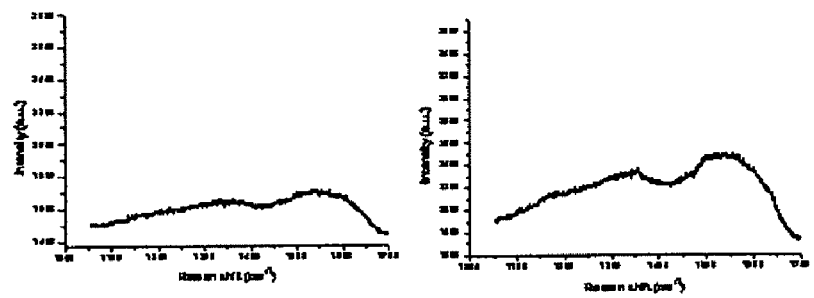

FIG. 4: showing specific detection of the complete viral RNA.

Figure 5:
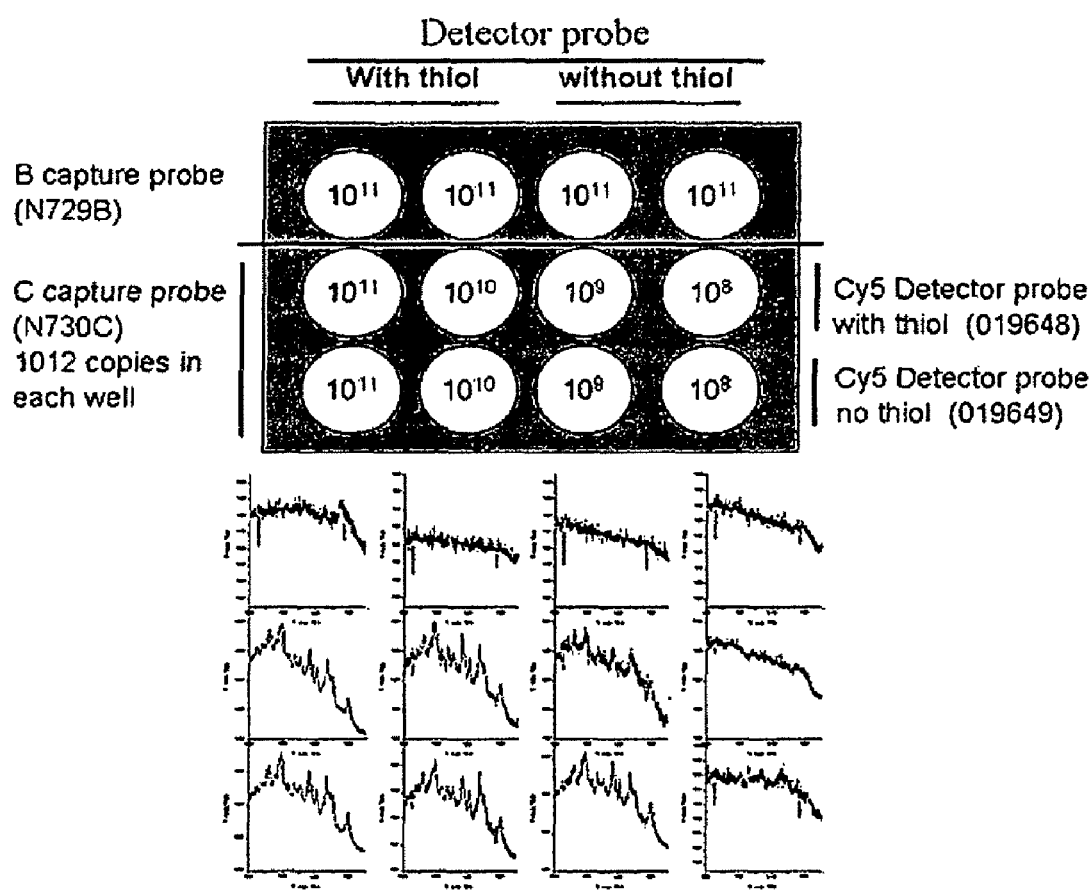

FIG. 5: showing detection of subtype-C viral DNA using Cy-5 tagged detector probe.

DETAILED DESCRIPTION OF THE INVENTION

Accordingly, the present invention relates to a high sensitivity assay for molecular typing of a biological sample using surface-enhanced Raman scattering (SERS) including resonance scattering (SERRS), wherein said assay comprising steps of:
a) extracting nucleic acid from the biological sample;
b) capturing the extracted nucleic acid in a microarray format using subtype-specific and window-specific capture probe(s); and
c) detecting the captured nucleic acid with a detector probe tagged to a reporter to determine molecular typing, subtypes and recombinants on the basis of pattern of signals generated.

In yet another embodiment of the present invention, the biological sample is selected from a group comprising infectious agents, disease causing agents, microorganisms, higher forms of life including human beings.

In still another embodiment of the present invention, the infectious agents are selected from a group comprising bacteria, viruses, fungi, protozoa and parasites.

In still another embodiment of the present invention, the viruses are selected from a group comprising helical viruses, icosahedral viruses, enveloped viruses and complex viruses, preferably HIV.

In still another embodiment of the present invention, the nucleic acid is either DNA or RNA.

In still another embodiment of the present invention, the capture probes are an array of oligonucleotides spotted in an array fashion on surface of an appropriate glass slide.

In still another embodiment of the present invention, the detector probes are adsorbed onto silver nanoparticles for further enhancement of the assay.

In still another embodiment of the present invention, the reporter is selected from a group comprising Raman reporter, fluorescent dye, radio-isotope and an enzyme.

In still another embodiment of the present invention, the reporter is Raman reporter selected from a group comprising Rhodamine, Cy-5, TAMRA and DSNB.

In still another embodiment of the present invention, the Raman reporter is preferably Rhodamine and Cy-5.

In still another embodiment of the present invention, the assay is applicable without amplification of the nucleic acid.

In still another embodiment of the present invention, the assay avoids false-positive/false-negative results and is inexpensive.

In still another embodiment of the present invention, the assay detects single nucleotide polymorphism in all types of organisms including human beings.

The present invention also relates to a high sensitivity assay for molecular typing of HIV using surface-enhanced Raman scattering (SERS) including resonance scattering (SERRS), wherein said assay comprising steps of:
a) extracting nucleic acid from the HIV;
b) capturing the extracted nucleic acid in a microarray format using subtype-specific and window-specific capture probe(s); and
c) detecting the captured nucleic acid with a detector probe tagged to a reporter to determine molecular typing, subtypes and recombinants on the basis of pattern of signals generated.

The present invention also relates to capture probes of SEQ ID NO: 1, SEQ ID NO: 2 and SEQ ID NO: 3 for capturing nucleic acid isolated from biological sample, wherein the capture probes are sub-type specific and window specific.

In still another embodiment of the present invention, the capture probes are an array of oligonucleotides spotted in an array fashion on surface of an appropriate glass slide.

In still another embodiment of the present invention, the oligonucleotides are synthesized in situ on glass surface using photolithography or pre-synthesized oligonucleotides selected from a group comprising succinylated oligonucleotides, 5' end amino-modified oligonucleotides, disulfide-modified oligonucleotides and other oligonucleotides linked through hetero-bi-functional cross-linking molecules to the surface are used.

In still another embodiment of the present invention, the nucleic acid is either DNA or RNA.

In still another embodiment of the present invention, the biological sample is selected from a group comprising infectious agents, disease causing agents, microorganisms, higher forms of life including human beings.

In still another embodiment of the present invention, the infectious agents are selected from a group comprising bacteria, viruses, fungi, protozoa and parasites.

In still another embodiment of the present invention, the viruses are selected from a group comprising helical viruses, icosahedral viruses, enveloped viruses and complex viruses, preferably HIV.

In still another embodiment of the present invention, the detector probe is non-specific and identifies all subtypes.

In still another embodiment of the present invention, the nucleic acid is either DNA or RNA.

The present invention also relates to a kit for molecular typing of biological sample using surface-enhanced Raman scattering (SERS) including resonance scattering (SERRS), wherein the kit comprising:

a) reagents and buffers to extract nucleic acid from the biological sample;
b) capture probes to capture the nucleic acid;
c) microarray plate to spot capture probes;
d) detector probe to detect capture probe;
e) reporter, preferably Raman reporter; and
f) device to detect pattern of signals generated from microarray.

In still another embodiment of the present invention, the kit comprise capture probes of SEQ ID NO: 1, SEQ ID NO: 2 and SEQ ID NO: 3 which are sub-type specific and window specific.

In still another embodiment of the present invention, the kit comprise the detector probe of SEQ ID NO: 4 which is non-specific and identifies all subtypes.

The present invention also relates to a method of manufacturing a kit for molecular typing of biological sample using surface-enhanced Raman scattering (SERS) including resonance scattering (SERRS), wherein the method comprising:
a) providing reagents and buffers in the kit to extract nucleic acid from the biological sample;
b) providing appropriate capture probes in the kit to capture the extracted nucleic acid;
c) providing microarray plate in the kit to spot the capture probes;
d) providing detector probe in the kit to detect the capture probe;
e) providing reporter, preferably Raman Reporter; and
f) providing device to detect pattern of signals generated from microarray to manufacture the kit.

An ideal strategy for the molecular subtyping of the HIV-1 strains must have all or several of the following properties.
1. The technique should not require target template amplification. This will be less expensive and circumvent the contamination problem. The technique should directly detect the viral RNA isolated from a biological sample.
2. The technique should have broader application in that it should be capable of detecting all the diverse viral subtypes in multiple windows.
3. The technique must avoid application of expensive fluorescent detection technology, unlike the real-time PCR that employs TaqMan probes chemically conjugated to fluorescent dyes.
4. The technique must exploit a powerful strategy for target detection especially compensating for the lack of target amplification.

We identified a novel and innovative strategy that satisfies the above requirements and molecularly characterize a viral subtype. Our strategy is based on capturing the viral RNA using a capture probe and detecting the latter with a reporter probe. An array of oligo-nucleotides that are subtype-specific and window-specific are amino-modified at the 5' end and are spotted in an array fashion on the surface of a silane-modified glass slide (Guo et al., 1994; Joos et al., 1997; Kumar et al., 2000; Lindroos et al., 2001). The capture probes are designed to target 5-10 individual windows spanning the entire length of the virus each window consisting of 1000 bp. The viral RNA extracted from a biological sample is directly captured in a series of the windows of the microarray depending on the molecular nature of the viral subtype. The captured viral RNA is detected using one or a pool of two or three detector probes that are tagged with a reporter molecule, a radio-isotope, fluorescent dye or a Raman reporter (RR). In the present example/invention, we employed a few fluorescent dyes as Raman Reporters as their vibrational properties can be detected by Raman spectroscopy using SERS/SERRS. Chemicals without a fluorescent property, such as 5,5'-dithio-bis succinimidyl-2-nitrobenzoate) (DSNB), can also be employed as Raman reporters in the present invention. In the present invention, we, however, use the name Raman reporter exclusively for fluorescent dyes like Rhodamine, TAMRA and others. The detector probes are highly conserved and detect all the diverse viral subtypes regardless of the subtype identity. The assay is characterized by moderate sensitivity when isotope- or fluorophore-labeled detector probe is used. However, the assay attains high sensitivity when the detector probes are tagged to a Raman reporter as the latter can exploit the phenomenon of surface-enhanced Raman scattering (SERS) or surface-enhanced Raman resonance scattering (SERRS) (Kneipp et al., 2002; Vo-Dinh et al., 2005; Xie et al., 2006). The high sensitivity of RR-tagged reporter probe functionally compensate for the lack of template amplification in our strategy.

The reporter probe/detector probe is linked to a Raman reporter, fluorescent dye, radio-isotope, an enzyme or several other such reporter molecules. Further, the detector probe is adsorbed onto the silver nanoparticles which functions as an enhancement factor and doesn't hinder Raman signal emission.

The capture probes are synthesized in situ on the glass surface in a spatially addressable manner using standard photolithography. Alternatively, presynthesized oligonucleotide are captured by several of the available chemistries. Oligonucleotides modified with an amino group are immobilized onto epoxy-silane-derivatised or isothiocyanate coated glass slides. Succinylated oligonucleotides can be coupled to aminophenyl- or aminopropyl-derivatised glass slides by peptide bonds. Disulfide-modified oligonucleotides can be immobilized onto a mercaptosilanised glass support by a thiol/disulfide exchange reaction. Many more attachment strategies using heterobifunctional crosslinking molecules giving many alternatives to the linking molecule and to the surface can be exploited.

Our strategy is innovative in immobilizing the intact viral RNA molecule, extracted from a biological sample, to an array of subtype- and window-specific capture probes and detecting the viral RNA using a RR-tagged reporter probe(s) and exploiting the phenomenon of SERS or SERRS for a sensitive detection and determination of the viral molecular nature based on the pattern of signals generated from the microarray (FIG. 1).

The invention is further elaborated with the help of following examples. However, these examples should not be construed to limit the scope of the invention.

EXAMPLE 1

Preparation of the Target Viral Nucleic Acids for Capture

Experiments were conducted using full-length or partial segments of viral RNA or DNA, single-stranded or double-stranded. To make full-length viral RNA, plasmid DNA containing full-length viral sequences were transfected into HEK293 cells using standard calcium phosphate precipitation technique (Jordan M et al. (2004) *Methods* 33:136) Culture medium was collected at 72 h and saved in aliquots in a deep freezer. Concentration of the viral antigen p24 in the culture medium (viral stock) was determined using a commercial kit (Perkin Elmer Life Sciences, Boston, Mass., USA). Alternatively, tissue culture infection dose 50 (TCID50) titers of the viral stocks were determined in TZM-bl cells essentially as described (e.g. at the website available at hiv.lanl.gov/content/nab-reference-strains/html/Clade-C/TZM-b-1_Assay-SOP_January2007.pdf). Viral RNA was released from the viral particles by adding the detergent NP-40 to the stocks to a final concentration of 1%. Viral RNA was extracted from the culture medium using paramagnetic beads and miniMag EXTRACTOR (bioMerieux, e.g. as described on the website at biomerieux-usa.com. Alternatively, viral RNA was extracted using commercial kits from the plasma or stock preparations according to manufacturer's instructions (e.g., available from the qiagen.com website for DNeasy96Plant Kit). To make single-stranded viral DNA representing a defined window of a given viral subtype, a previously published protocol was used (Knuchel et al. (2000) *J. Histochem Cytochem* 48:285. Viral molecular clones representing viral subtypes were obtained from The National Institutes of Health AIDS Research and Reference Reagent Program (at the website available at aidsreagent.org/about_program.cfm). The following viral molecular clones were used in the experiments to represent defined viral subtypes, p92RW009.6 (#4006) for subtype-A, pYU-2 (#1350) and pNL4-3 (#114) for subtype-B and p93IN904 (#3958) for subtype-C.

EXAMPLE 2

Design and Synthesis of the Oligonucleotide Probes

The full-length HIV-1 sequences were down loaded from the Los Alamos database (available at hiv.lanl.gov/content/hiv-db/mainpage.html) and aligned using CLUSTAL X with minor manual adjustments (Thompson J D, Gibson T J, Plewniak F, Jeanmougin F, Higgins D G. The CLUSTAL_X windows interface: flexible strategies for multiple sequence alignment aided by quality analysis tools. Nucleic Acids Res 1997; 25 (24): 4876-4882). Regions that are highly conserved within a given viral subtype and deviated by at least one base pair from all other subtypes were identified by visual inspection. Oligonucleotides of 20-25 bp were designed using Oligo software version-6 to serve as capture or detector probes (available at oligo.net/). Oligonucleotide synthesis along with chemical modification and fluorescent dye tagging has been ordered from a few commercial companies that offer custom services including AlphaDNA, MWG and Sigma-Aldrich.

EXAMPLE 3

Sequences of Probes Used in the Experiments (All the Sequences from the Anti-Sense Strand)

EXAMPLE 4

Subtype-C Capture Probe Captures Subtype-C, but not -A or -B, Viral DNA

Amino-modified subtype-C capture probe (N730c) was captured to silane-modified glass surface. Single-stranded DNA within the LTR region of the virus derived from 3 different viral subtypes A, B or C, was added to the capture probe at numbers shown above the wells. After washing to remove unbound viral DNA, the wells were incubated with the detector probe N707 that was tagged with Rhodamine-6-G (R6G). Following incubation and washing, the wells were incubated with silver nanoparticles and the Raman signal was acquired for one second. The data have been presented in (FIG. 2). The slide on which capture probe was deposited was shown in the left panel with the number of viral DNA molecules indicated above the columns in FIG. 2. The right-hand panel presents data obtained. The capture probe immobilized only the subtype-C DNA (top row) but not subtypes-A or B (middle and bottom rows, respectively) confirming the specificity of the capture probe. While the total area of the spot where the capture probe is immobilized is approximately $3.1 \times 10^{-6}$ $M^2$ (2 mm×2 mm), the area scanned in SERS is only one millionth of the total area $1.2 \times 10^{-13}$ $M^2$ (4 μM×4 μM). This area is equivalent to approximately $10^4$ viral DNA molecules in the top most and left most panel where $10^{10}$ copies were actually used. This experiment confirmed that the present strategy can specifically detect target nucleic acid molecules without PCR amplification with high sensitivity.

EXAMPLE 5

Capture Probes are Specific to Viral Subtypes

The following experiment, using a non-SERS detection strategy, confirmed that subtype-specific probes specifically identify intended viral target nucleic acids efficiently. In this experiment, one capture probe for HIV-1 subtype-B (N729b) and two different probes for subtype-C (N730c and N731c) were used independently. A-detector probe (N707) was end-labeled with radio-isotope $^{32}P$ using standard molecular techniques. The detector probe must bind to all viral strains regardless of subtype differences. Single-stranded DNA derived from the LTR region of subtype-B or -C viruses was used, each at $2 \times 10^{13}$ copies, in the experiment. Following a

| Probe | Comment | Sequence (5'-3') | Coordinate |
|---|---|---|---|
| SEQ ID No. 4 (N707) | 1) Detector probe in U5-LTR<br>2) Identifies all subtypes<br>3) Modifications<br>   a) None<br>   b) Cy-5 (19649)<br>   c) R6G<br>   d) Thiol and Cy-5 (19648) | AGTTACCAGAGTCACACAACAGACGG | 564-589<br>HXB2 |
| SEQ ID No. 1 (N729b) | 1) Subtype-B capture probe<br>2) Amino-modified at N-term<br>3) Spanning the Sp1 sites | CCAGTCCCGCCCAGGCCACG | 381-400<br>HXB2 |
| SEQ ID No. 2 (N730c) | 1) Subtype-C capture probe<br>2) Amino-modified at N-term<br>3) Located spanning the C-kB | ACCTCCTGGAACGCCCCAGT | 363-382<br>Indie |
| SEQ ID No. 3 (N731c) | 1) Subtype-C capture probe<br>2) Amino-modified at N-term<br>3) Located in 'R' of LTR | TCAGATCTGGTCTACCTAGAGAGAC | 456-480<br>Indie | series of hybridizations and washing, the slides were exposed to X-ray films and an autoradiogram was developed. The results (FIG. 3) demonstrate that subtype-B specific capture probe binds only subtype-B DNA but not subtype-C DNA. In a similar fashion, both the subtype-C specific capture probes capture only subtype-C, but not -B, DNA. The non-SERS detection strategy thus confirmed specific binding of the designed probes only to homologous, but not heterologous, target nucleic acids even though they are closely related.

EXAMPLE 6

Capture and Detection of the Viral RNA from Culture Supernatant

The following experiment illustrates capture and detection of full-length viral RNA from the cell culture supernatant. Subtype-B molecular clone HXB-2 was cultured in the laboratory in T-cells using standard culture conditions. Virus was concentrated from 1 ml of the culture medium by high-speed centrifugation and resuspended in 0.1 ml of lysis buffer containing 1% NP-40 and 0.1% BSA and 5 µl of this solution was used in the experiment. Subtype-B specific capture probe N729b and -C specific probe N730c were used for the capture of the viral RNA. Detector probe N707 tagged to R6G was used for SERS detection. The results (FIG. 4) prove that, using the novel strategy it is possible to detect full-length viral RNA. Only the subtype-B specific capture probe (top panels) but not -C specific probe (bottom panels), detects the subtype-B virus.

EXAMPLE 7

Detection of Subtype-C Viral DNA with Cy-5 Tagged Detector Probe

We identified that Cy-5 fluorescent dye to be as good Raman Reporter as R6G for the novel detection strategy. In the following experiment, the top panel contains B-specific capture probe N729b that should not capture the C-viral DNA used in the experiment. The middle and bottom panels contain C-specific capture probe N730c. The detector probe 19649 (bottom panel) which must detect all the viral strains regardless of the subtype differences was tagged to Cy-5. The same probe was also chemically modified by adding an additional thiol group (and Cy-5) for efficient binding to the silver nano-particles. The variant probe is called 19648. The copy number of the subtype-C DNA used in the experiment is indicated. The data (FIG. 5) demonstrated that Cy-5 linked detector probe can identify subtype-C DNA with high efficiency (middle and bottom panels). B-specific capture probe doesn't detect the C-DNA confirming specificity (top panels). Presence of a thiol group in the detector probe doesn't seem to give an additional advantage as both the detector probes with and without thiol group show identical detection sensitivity (compare middle and bottom panels).

ADVANTAGES OF THE INVENTION

1. Does not require template amplification. False positive results are avoided. Economically inexpensive.
2. Broader range. A large number of capture probes can target several windows within the virus and essentially every viral subtype can be included in the detection strategy.
3. Highly sensitive detection. The reporter probe is conjugated to a Raman reporter hence exploiting the phenomenon of SERS or SERRS there by a single molecule detection should be possible theoretically. The technique here uses SERRS, where both surface enhancement as well as resonant enhancement are employed, making this technique highly sensitive to detect a small number of detector probe molecules. Our strategy of generating the reporter signal by adsorbing the probe onto the silver nanoparticle is far superior to the alternative technique commonly employed where the RR is coated with thin layer of silver. Our strategy is superior in terms of both signal enhancement as well as effects of absorption coefficient of silver.

Application of Raman reporters also offers the advantage of employing low output LASERs and/or diode lasers that are less expensive. Technically less complicated and less expensive equipment could be designed.

Our strategy of microarray capture of the nucleic acid template blended with SERRS-mediated detection have wider global application where HIV-1 infections are common. The diverse viral subtypes of HIV-1, presently known recombinant viruses and recombinant strains that may arise in future can be detected efficiently. Determination of the HIV-1 molecular nature will be important in the following areas and can have significant impact on treatment decisions, and intervention strategies.
1) Basic research where determination of the subtype and/or recombinant nature of viruses is required
2) Drug therapy, where drug resistant mutants should be quickly identified
3) Vaccine studies, where a knowledge of the viral strains in a given population or geographical region is essential Importantly, the strategy we developed have a universal application where genetic diversity is a serious problem with other infectious organisms including HIV-2, Influenza, Polio, Dengue, HBV, HCV, Dengue, several bacteria including Tuberculosis, parasites including malaria and other microorganisms. Additionally, the technique also finds application to SNP (single nucleotide polymorphism) in all types of organisms including the human beings. The strategy is technically less complicated and find broader application in resource poor conditions.

REFERENCE LIST

1) Abravaya K, Esping C et al, Performance of a multiplex qualitative PCR LCx assay for detection of human immunodeficiency virus type 1 (HIV-1) group M subtypes, group O, and HIV-2. *J Clin Microbiol,* 38, 716-723 (2000).
2) Barbosa E F, Carneiro-Proietti A B et al, HIV-1 detection and subtyping by PCR and heteroduplex mobility assay in blood donors: can these tests help to elucidate conflicting serological results? *Transfus Sci,* 19, 39-43 (1998).
3) Carr J K, Laukkanen T et al, Characterization of subtype A HIV-1 from Africa by full genome sequencing. *AIDS,* 13, 1819-1826 (1999).
4) Collins M L, Irvine B et al, A branched DNA signal amplification assay for quantification of nucleic acid targets below 100 molecules/ml. *Nucleic Acids Res,* 25, 2979-2984 (1997).
5) de Baar M P, Timmermans E C et al, One-tube real-time isothermal amplification assay to identify and distinguish human immunodeficiency virus type 1 subtypes A, B, and C and circulating recombinant forms AE and AG. *J Clin Microbiol,* 39, 1895-1902 (2001).
6) Delwart E L, Shpaer E G et al, Genetic relationships determined by a DNA heteroduplex mobility assay: analysis of HIV-1 env genes. *Science,* 262, 1257-1261 (1993).
7) Desire N, Dehee A et al, Quantification of human immunodeficiency virus type 1 proviral load by a TaqMan real-time PCR assay. *J Clin Microbiol,* 39, 1303-1310 (2001).
8) Espy M J, Uhl J R et al, Real-Time PCR in Clinical Microbiology: Applications for Routine Laboratory Testing. *Clin Microbiol Rev,* 19, 165-256 (2006).

9) Gerhardt M, Mloka D et al, In-depth, longitudinal analysis of viral quasispecies from an individual triply infected with late-stage human immunodeficiency virus type 1, using a multiple PCR primer approach. *J Virol,* 79, 8249-8261 (2005).
10) Guo Z, Guilfoyle R A et al, Direct fluorescence analysis of genetic polymorphisms by hybridization with oligonucleotide arrays on glass supports. *Nucleic Acids Res,* 22, 5456-5465 (1994).
11) Herbinger K H, Gerhardt M et al, Frequency of HIV type 1 dual infection and HIV diversity: analysis of low- and high-risk populations in Mbeya Region, Tanzania. *AIDS Res Hum Retroviruses,* 22, 599-606 (2006).
12) Heyndrickx L, Janssens W et al, Simplified Strategy for Detection of Recombinant Human Immunodeficiency Virus Type 1 Group M Isolates by gag/env Heteroduplex Mobility Assay. *J Virol,* 74, 363-370 (2000).
13) Hoelscher M, Dowling W E et al, Detection of HIV-1 subtypes, recombinants, and dual infections in east Africa by a multi-region hybridization assay. *AIDS,* 16, 2055-2064 (2002).
14) Joos B, Kuster H and Cone R: Covalent attachment of hybridizable oligonucleotides to glass supports. *Anal Biochem,* 247, 96-101 (1997).
15) Kern D, Collins M et al, An enhanced-sensitivity branched-DNA assay for quantification of human immunodeficiency virus type 1 RNA in plasma. *J Clin Microbiol,* 34, 3196-3202 (1996).
16) Kneipp K, Kneipp H et al, Surface-enhanced Raman scattering and biophysics. *J Phys: Condens Matter,* 14, R597-R624 (2002).
17) Kumar A, Larsson O, Parodi D and Liang Z: Silanized nucleic acids: a general platform for DNA immobilization. *Nucleic Acids Res,* 28, E71 (2000).
18) Kwok S and Higuchi R: Avoiding false positives with PCR. *Nature,* 339, 237-238 (1989).
19) Lal R B, Chakrabarti S and Yang C: Impact of genetic diversity of HIV-lon diagnosis, antiretroviral therapy & vaccine development. *Indian J Med Res,* 121, 287-314 (2005).
20) Leitner T., B. Foley, B. Hahn, P. Marx, F. McCutchan, J. Mellors, S. Wolinsky and B. Korber: HIV Sequence Compendium 2005. In: Anonymous Theoretical Biology and Biophysics Group, Los Alamos National Laboratory, LA, (2005).
21) Lindroos K, Liljedahl U, Raitio M and Syvanen A C: Minisequencing on oligonucleotide microarrays: comparison of immobilisation chemistries. *Nucleic Acids Res,* 29, E69 (2001).
22) Luo C C, Downing R G et al, The development and evaluation of a probe hybridization method for subtyping HIV type 1 infection in Uganda. *AIDS Res Hum Retroviruses,* 14, 691-694 (1998).
23) Najera R, Delgado E, Perez-Alvarez L and Thomson MM: Genetic recombination and its role in the development of the HIV-1 pandemic. *AIDS,* 16 Suppl 4, S3-16 (2002).
24) Niesters H G: Quantitation of viral load using real-time amplification techniques. *Methods,* 25, 419-429 (2001).
25) Peeters M.: Recombinant HIV sequences: Their role in the global epidemic. In: HIV sequence compendium 2000, eds. C. Kuiken, B. Foley, B. Hahn, P. Marx, F. E. McCutchan, J. Mellors, J. Mullins, J. Sodroski, S. Wolinsky and B. Korber (Theoritical Biology and Biophysics Group, Los Alamos National Laboratory, Los Alamos, N. Mex., USA, Los Alamos) pp. 54-72 (2000).
26) Peeters M, Liegeois F et al, Subtype-specific polymerase chain reaction for the identification of HIV-1 genetic subtypes circulating in Africa. *AIDS,* 12, 671-673 (1998).
27) Robbins K E, Kostrikis L G et al, Genetic analysis of human immunodeficiency virus type 1 strains in Kenya: a comparison using phylogenetic analysis and a combinatorial meltingassay. *AIDS Res Hum Retroviruses,* 15, 329-335 (1999).
28) Rys P N and Persing D H: Preventing false positives: quantitative evaluation of three protocols for inactivation of polymerase chain reaction amplification products. *J Clin Microbiol,* 31, 2356-2360 (1993).
29) Scherczinger C A, Ladd C et al, A systematic analysis of PCR contamination. *J Forensic Sci,* 44, 1042-1045 (1999).
30) Van Harmelen J, van der Ryst E et al, Restriction fragment length polymorphism analysis for rapid gag subtype determination of human immunodeficiency virus type 1 in South Africa. *J Virol Methods,* 78, 51-59 (1999).
31) Vo-Dinh T, Yan F and Wabuyele MB: Surface-enhanced Raman scattering for medical diagnostics and biological imaging. *J Raman Spectroscopy,* 36, 640-647 (2005).
32) Wan Z, Wang Y et al, Development of array-based technology for detection of HAV using gold-DNA probes. *J Biochem Mol Biol,* 38, 399-406 (2005).
33) Wilke W W, Sutton L D and Jones R N: Automation of polymerase chain reaction tests to achieve acceptable contamination rates. *Clin Chem,* 41, 622-623 (1995).
34) Xie X S, Yu J and Yang W Y: Living cells as test tubes. *Science,* 312, 228-230 (2006).
35) Yeung A T, Holloway B P, Adams P S and Shipley G L: Evaluation of dual-labeled fluorescent DNA probe purity versus performance in real-time PCR. *BioTechniques,* 36, 266-5 (2004).

We claim:

1. A single-stranded capture probe consisting of the sequence set forth in SEQ ID NO: 1, SEQ ID NO: 2 or SEQ ID NO: 3 suitable for capturing nucleic acid isolated from an Human Immunodeficiency Virus (HIV), wherein the capture probe is viral sub-type specific and window specific.

2. An array of oligonucleotides spotted in an array fashion on a surface of an appropriate glass slide comprising the capture probe of claim 1.

3. The array of claim 2, wherein the oligonucleotides are synthesized in situ on a glass surface using photolithography or pre-synthesized oligonucleotides selected from the group consisting of succinylated oligonucleotides, 5' end amino-modified oligonucleotides, disulfide-modified oligonucleotides, and oligonucleotides linked through hetero-bi-functional cross-linking molecules.

4. The capture probe of claim 1, wherein the nucleic acid is DNA or RNA.

5. A single-stranded detector probe consisting of the sequence set forth in SEQ ID NO: 4 suitable to detect captured nucleic acid, wherein the detector probe is non-specific and identifies all viral subtypes.

6. The detector probe of claim 5, wherein the nucleic acid is DNA or RNA.

7. A kit for molecular typing of Human Immunodeficiency Virus (HIV) using surface-enhanced scattering (SERS) including resonance scattering (SERRS), wherein the kit comprises:
   a) reagents and buffers to extract nucleic acid from the HIV;
   b) one or more single-stranded probes to capture nucleic acid, selected from the group consisting of the sequence set forth in SEQ ID NO: 1, SEQ ID NO: 2 and SEQ ID NO: 3;
   c) a microarray plate to spot the capture probes;
   d) a single-stranded detector probe consisting of the sequence set forth in SEQ ID NO: 4 to detect captured nucleic acid; and
   e) a reporter.

8. The kit of claim 7, wherein the capture probes of SEQ ID NO: 1, SEQ ID NO: 2 and SEQ ID NO: 3 are viral sub-type specific and window specific.

9. The kit of claim 7, wherein the detector probe of SEQ ID NO: 4 is non-specific and identifies all viral subtypes.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: synthetic subtype-B capture probe N729b
<220> FEATURE:
<221> NAME/KEY: modified_base
<222> LOCATION: (1)..(1)
<223> OTHER INFORMATION: c modified by amino group

<400> SEQUENCE: 1

```
ccagtcccgc ccaggccacg                                          20

<210> SEQ ID NO 2
<211> LENGTH: 20
<212> TYPE: DNA
<213> ORGANISM: Artificial
<220> FEATURE:
<223> OTHER INFORMATION: synthetic subtype-C capture probe N730c
<220> FEATURE:
<221> NAME/KEY: modified_base
<222> LOCATION: (1)..(1)
<223> OTHER INFORMATION: a modified by amino group

<400> SEQUENCE: 2
acctcctgga acgccccagt                                          20

<210> SEQ ID NO 3
<211> LENGTH: 25
<212> TYPE: DNA
<213> ORGANISM: Artificial
<220> FEATURE:
<223> OTHER INFORMATION: synthetic subtype-C capture probe N731c
<220> FEATURE:
<221> NAME/KEY: modified_base
<222> LOCATION: (1)..(1)
<223> OTHER INFORMATION: t modified by amino group

<400> SEQUENCE: 3
tcagatctgg tctacctaga gagac                                    25

<210> SEQ ID NO 4
<211> LENGTH: 26
<212> TYPE: DNA
<213> ORGANISM: Artificial
<220> FEATURE:
<223> OTHER INFORMATION: synthetic detector probe N707

<400> SEQUENCE: 4
agttaccaga gtcacacaac agacgg                                   26
```